United States Patent [19]
Bonpard et al.

[11] Patent Number: 5,797,741
[45] Date of Patent: Aug. 25, 1998

[54] DENTAL IMPLANT ARTICLE AND DEVICE FOR FITTING IT

[76] Inventors: Bruno Bonpard, 7 rue Valentin Haüi; Elisabeth Mauduech, 7 rue Valentin Haüy, both of Paris, France, 75015

[21] Appl. No.: 737,784
[22] PCT Filed: May 29, 1995
[86] PCT No.: PCT/FR95/00692
§ 371 Date: Nov. 25, 1996
§ 102(e) Date: Nov. 25, 1996
[87] PCT Pub. No.: WO95/32682
PCT Pub. Date: Dec. 7, 1995

[30] Foreign Application Priority Data

May 31, 1994 [FR] France .................... 94 06593

[51] Int. Cl.[6] ...................... A61C 3/00; A61C 8/00
[52] U.S. Cl. ............................ 433/75; 433/173
[58] Field of Search ................... 433/75, 76, 173, 433/174, 176

[56] References Cited

U.S. PATENT DOCUMENTS

| | | | |
|---|---|---|---|
| 3,474,537 | 10/1969 | Christensen | 433/174 |
| 3,919,772 | 11/1975 | Lenczycki | 433/173 |
| 3,981,079 | 9/1976 | Lenczycki | 433/173 |
| 4,872,840 | 10/1989 | Bori | 433/173 |
| 5,320,529 | 6/1994 | Pompa | 433/76 |
| 5,542,847 | 8/1996 | Marguiles | 433/174 |

*Primary Examiner*—John J. Wilson
*Attorney, Agent, or Firm*—Larson & Taylor

[57] ABSTRACT

A dental implant article includes an implant stem for insertion into a substantially vertical cavity drilled in the maxillary bone. The implant stem includes at least one bore substantially transverse to its axis. A cylindrical key with a cross section corresponding to that of the bore is inserted into the maxillary bone and in the implant stem which was previously positioned. A fitting device for drilling of the bone is also provided.

20 Claims, 2 Drawing Sheets

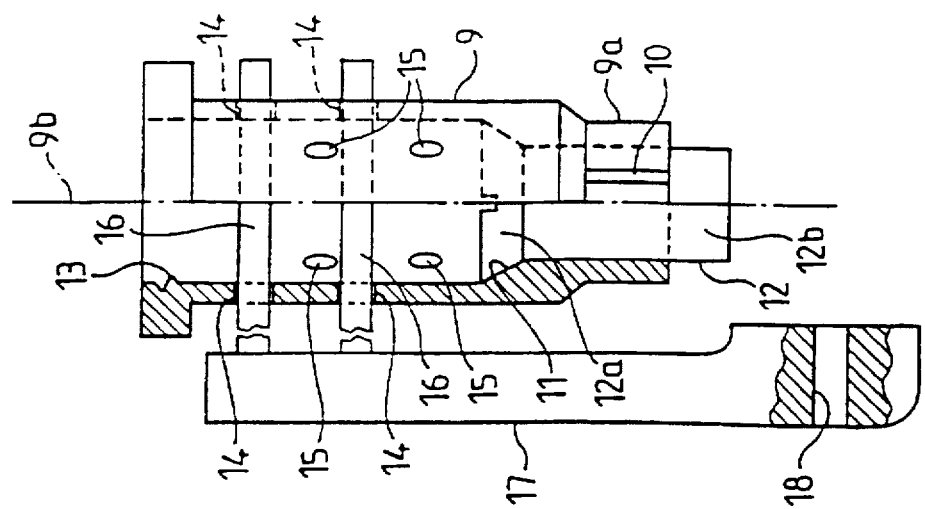
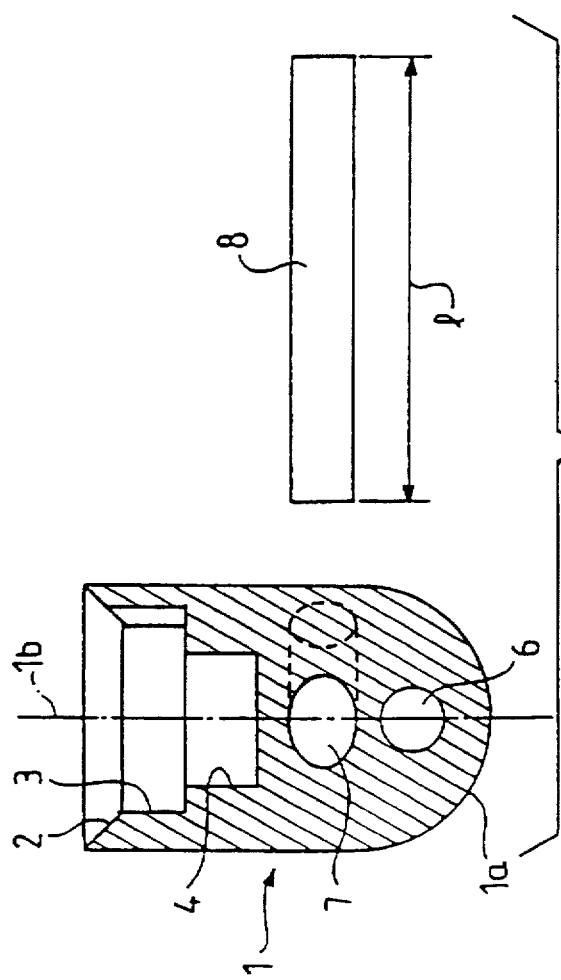
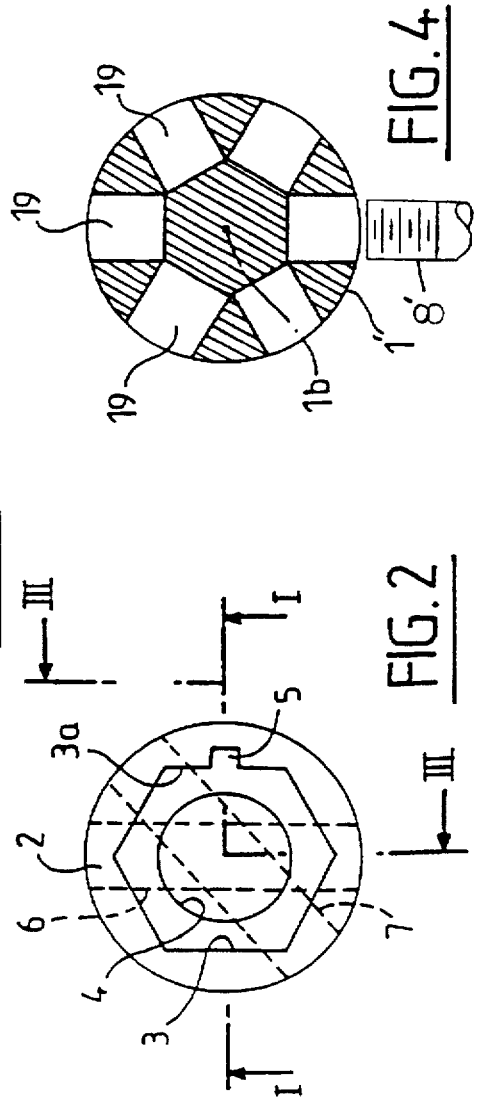
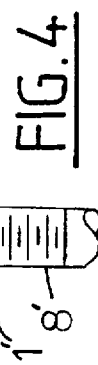

DENTAL IMPLANT ARTICLE AND DEVICE FOR FITTING IT

FIELD OF THE INVENTION

The present invention relates to dental implants and, more particularly, to a dental implant article having an implant body intended to be fitted in a substantially vertical cavity drilled into the jawbone from the upper face (or osseous crest) of the latter.

The invention also relates to a device which is especially designed for fitting the dental implant article.

BACKGROUND OF THE INVENTION

Implant articles which are currently used consist of a cylindrically shaped implant body fitted by simple insertion or by screwing into the jawbone in the natural axis of the tooth after a pit (or cavity) with the dimension of the implant has been drilled.

However, implants of this type have limited lifetimes, on the one hand because of the anatomy of the jawbones (these bones being formed by a superficial layer of hard bone, referred to as cortical bone, surrounding a much softer spongy bone region) and, on the other hand, because of the large mechanical stresses applied to the cortical bone by these implants as a result of mastication.

With the aim of extending the implant lifetime, an implant article has already been proposed which is designed for producing T-shaped or cross-shaped implants. This article comprises a fluorinated plastic plate which is inserted laterally into the bone via a previously hollowed cavity parallel to the gingival crest, and a rod-shaped implant body intended to be inserted axially into an osseous pit also hollowed beforehand into the jawbone. This pit is positioned in such a way that the plate crosses it. This plate has a tap formed at its center. The implant body is screwed into the tap.

Because of the purchase which it offers on the upper cortical bone, as well as on the lower and outer cortical bones, this T-shaped implant has the advantage of offering an increased support area on the hard bone, making it possible to minimize the pressures exerted on this cortical bone by the implant during mastication. Nevertheless, given that it is necessary to produce lateral cuts which extend far enough to allow the transverse plate to pass through, fitting this known implant is complicated, inexact and above all very damaging to the bone.

Furthermore, this implant design cannot be applied to small implants, or to the cases when an implant is to be installed in a bone with small volume or low density.

In order to solve the drawbacks of various means for lateral attachment of an implant in the jawbone, U.S. Pat. No. 3,981,079 has also proposed to produce one or more tapped transverse passages in the implant, through which self-tapping threaded rods are screwed. To this end, a drilling template is temporarily secured to the implant and a hole is drilled through the bone, which hole extends the said passage on each side of the implant, after which the threaded rod is screwed into the hole and through the tapped passage. This solution is difficult to employ and would require a large number of templates. Above all, however, it is extremely harmful to the bone and does not ever seem to have been put into practice.

SUMMARY OF THE INVENTION

The invention overcomes these drawbacks and its object is, in particular, to propose an implant article for producing an implant which, while bearing on the upper and lateral cortical bones, avoids the drilling of large cavities in the direction transverse to the dental axes.

According to the invention, this object is achieved by the fact that the implant body is provided with at least one bore substantially transverse to its axis; and by the fact that use is made of at least one cylindrical key as the transverse element which makes it possible to support the implant on the lateral cortical bones, the cross-section of which key corresponds substantially to that of the bore of the implant body. This key is intended to be introduced into the jawbone through holes drilled beforehand laterally into this bone. It is intended to be accommodated in the bore of the implant.

Thus, fitting the implant produced by means of the implant article according to the invention only requires small-diameter lateral holes to be drilled for passage of the key, while this implant also has the advantage of bearing both on the upper cortical bone (via the implant body) and on the lateral cortical bones (via the key) and the implant body.

Furthermore, since the mechanical linkage between the implant body and the transverse element (the key) is a linkage effected by passing one of the parts (the key) through the bulk of the other (the implant body), the implant body is therefore securely locked in rotation about its axis (which corresponds to the axis of the pit in which it is accommodated); in other words, the implant body cannot pivot on itself.

Furthermore, the implant article according to the invention affords the practitioner the opportunity of adapting to the particular situation of the bone which he encounters, with a view to obtaining the best result in terms of quality of purchase. He may, for example, adopt a procedure whereby the key passes through a maximum compact bone thickness by suitably choosing the angular orientation of the implant body (and therefore that of the bore with which the latter is provided) relative to the jawbone. Since it is smooth, the key slides easily into the holes drilled beforehand into the bone, and in or through the transverse bore provided in the implant.

The effect of these factors is that the implant article according to the invention permits, at the same time, extension of indications to small-dimension implants, and to the cases of a bone with small volume or low density, faster loading of the implant, a longer implant lifetime, possible use of the keying to form the space required for an artificial membrane which would be used for guided osseous regeneration of the site of the implantation, secure immobilization of an implant which can be used immediately in a dental extraction site, and particularly favorable bone integration conditions.

It is advantageous for the bore of the implant body to be a bore which passes fully through the implant body, and for the key to be dimensioned so that it extends from the outer cortical bone to the inner cortical bone.

In order to allow the practitioner to adapt to the morphology of his patient, it is advantageous to provide him with a set of several keys with the same cross-sectional dimension and shape but with different lengths. The practitioner will thus be able to select from these keys the one whose length corresponds substantially to the thickness of the jawbone measured in the horizontal direction.

According to a preferred embodiment of the invention, use is made of a plurality of keys for producing an implant, the implant body being provided with a plurality of bores which can be oriented in parallel directions, or alternatively in different directions, and located in different planes transverse to the axis of the implant in such a way that they do not meet.

The invention also relates to a particular instrument for fitting the dental implant article according to the invention in the jawbones. According to the invention, this instrument includes a positioning member designed especially to be fixed on the implant body with particularly precise positioning relative to the latter while being laterally adjustable relative to the bone in which the implant is accommodated, and therefore relative to the implant, so that it can be applied, preferably by sliding, against the bone to be drilled. This positioning member has the purpose of acting as a support for a drilling template which is intended to guide, relative to the implant body, the bit which will be used for drilling the lateral hole or holes intended for implanting the key (or keys).

This positioning member may advantageously be positioned and fastened on the implant by using the positioning and fastening means already provided on the implant in order to accommodate the dental prosthesis to be fixed on the implant.

According to a currently preferred embodiment, the positioning member is produced in the form of a tube which has a straight axis and is open at both ends. It has an end part with a cross-section designed and dimensioned to be fitted into an axial recess, of corresponding cross-section and open at the top, formed in the implant body. On one of its faces, the end part has a relief, projection or recess intended to interact with a correspondingly shaped relief, recess (or projection) provided in the wall of the recess of the implant body. The later arrangement serves as an "orienter" which prevents any error in angular positioning between the positioning tube and the implant body.

In its recess, the positioning tube has a conical bearing surface for the countersunk head of a screw whose threaded shank extends out of the tube at the end which, for example, has a polygonal part. This threaded shank is intended to be screwed into a corresponding tapped blind axial bore formed in the implant body after the recess of polygonal cross-section. It is advantageous for the screw to be made captive by providing a deformation in the inner wall of the positioning tube, which destination forms an abutment preventing the screw head from emerging out of the tube.

Still according to this preferred embodiment, the tubular positioning member has holes, transverse to its axis, which are intended to accommodate, by sliding, but without play, tenons (or rods) for positioning the drilling template. The latter furthermore has a passage, or drilled hole, intended to be used as a guide for the bit for drilling the lateral holes of the jawbone. The axis of this drilled hole is advantageously parallel to the positioning tenons.

This passage is preferably made in a tubular element whose free end is chamfered so that it can pass through the gingiva and be applied directly against the vertical part of the bone.

BRIEF DESCRIPTION OF THE DRAWINGS

Other advantages and characteristics of the invention will emerge from reading the following description of two embodiments, which description is given with reference to the appended drawings, in which:

FIG. 1 is a view in elevation and in vertical section, on the plane I—I in FIG. 2, of an implant body and a key in the mounting position, according to one embodiment of the invention;

FIG. 2 is a plan view of the implant body in FIG. 1;

FIG. 3 is a view in elevation and in half longitudinal section, on a plane corresponding to the plane III—III in FIG. 2, of a positioning tube on which a drilling template is mounted in the working position, these elements being represented on a scale which is slightly reduced compared to that of the representation of the implant body and the key in FIGS. 1 and 2; and FIG. 4 is a horizontal section through an implant body according to a second embodiment of the invention;

DESCRIPTION OF THE PREFERRED EMBODIMENTS

Figure 5:
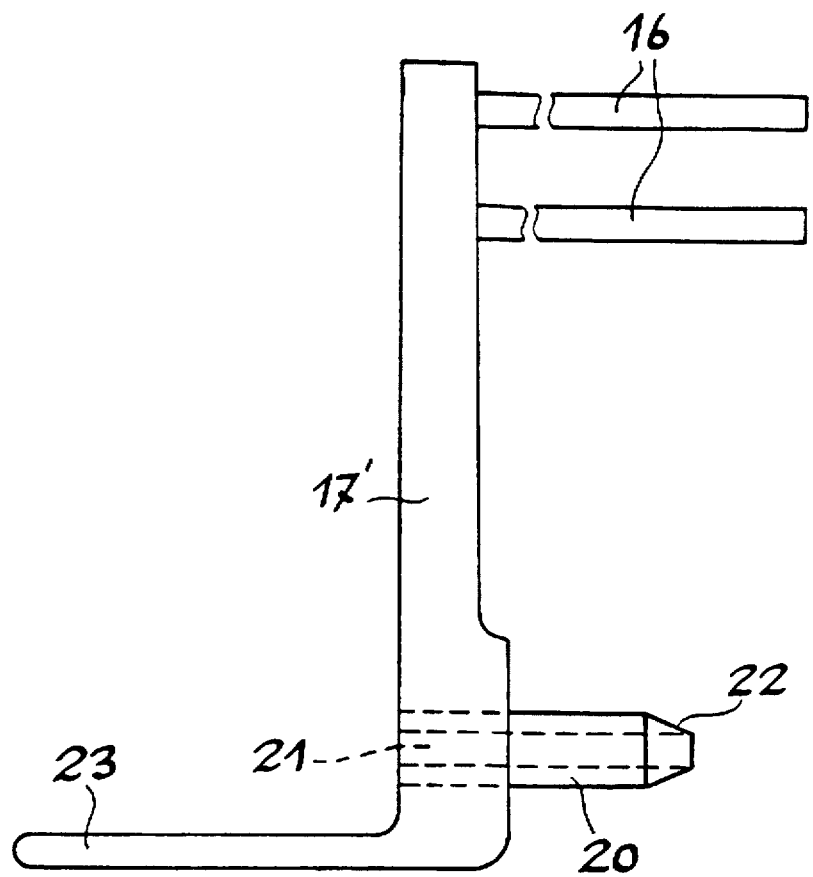
FIG. 5 is a view in elevation of a positioning template according to an improved embodiment of the invention.

The implant body 1 represented in FIGS. 1 and 2 has a cylindrical shape of circular cross-section. The lower end 1a of the body is rounded, for example in a hemispherical shape.

The upper end of the implant 1 has a blind axial recess which is open at the top and is composed of three successive contiguous segments, namely, from top to bottom: a conical flaring 2, a cylindrical segment of regular hexagonal cross-section 3, and a tapped cylindrical segment 4 of circular cross-section.

One of the faces 3a of the hexagonal segment 3 is provided with an axial groove 5 whose purpose will be explained further on.

The lower part of the body 1 has two through-bores 6 and 7, the axes of which are perpendicular to the axis 1b of the body 1. The bores 6 and 7, which are located at different heights and have angular orientations which differ from one to the other, are each intended to receive a key 8 represented in the mounting position in FIG. 1.

The key 8 has a length 1 which is sufficient to extend from the outer cortical bone to the inner cortical bone, passing through a bore 6, 7 of the body 1.

In order to allow the practitioner to adapt to the morphology of his patient, it is advantageous to provide him with a set of several keys with the same transverse dimensions but with different lengths. The practitioner will thus be able to select from these keys the one whose length corresponds substantially to the thickness of the jawbones measured in the horizontal direction.

The recess 2, 3, 4 of the body 1 is, of course, intended to accommodate parts or prostheses which are known per se. In the context of the present invention, this recess has been designed especially so that it can accommodate an alignment and drilling template device which will now be described with reference to FIG. 3.

As can be seen in FIG. 3, the alignment and drilling template device comprises a tubular alignment part 9 which has a straight axis and is open at both ends. The part 9 has an end part 9a which has a regular polygonal cross-section, this part being designed and dimensioned so that it can be fitted into the axial recess 3, of corresponding polygonal cross-section, formed in the implant body 1.

On one of its faces, the end part 9a has a rib 10 intended to be engaged in the correspondingly shaped groove 5 provided in the face 3a of the polygonal recess 3 of the implant body 1. This interaction between the members 5 and 10 makes it possible to locate the angular position of the part 9 relative to the body 1, thus producing an "orienter" making it possible to avoid any error in angular positioning between the positioning tube 9 and the implant body 1.

The inner wall of the positioning tube 9 has a conical bearing surface 11 for the countersunk head 12a of a screw 12, the threaded shank 12b of which extends downwards out of the tube 9, at the end with the polygonal part 9a. This threaded shank 12b is intended to be screwed into the tapped blind axial bore 4 formed in the implant body 1 after the recess 3 of polygonal cross-section.

The screw 12 is made captive by creating a deformation 13 in the inner wall of the positioning tube 9, this deformation forming an abutment preventing the screw head 12a from emerging out of the tube 9.

The tubular positioning member 9 has two sets of holes 14, 15, transverse to its axis 9b, which are intended to receive, without play, tenons (or rods) 16 for positioning a drilling template 17. The latter furthermore has a bore 18 intended to be used as a guide for the bit of a drill (not shown) used for drilling the lateral holes of the jawbone. As shown by FIG. 3, the axis of the bore 18 is parallel to the positioning tenons 16.

Each set of holes 14, 15 corresponds to the height and to the orientation corresponding to the bores, 6 and 7 respectively, of the body 1 fitted in the bone of the jaw. For drilling the bone, the practitioner exclusively makes use of the guide bore 18 whose diameter is equal to that of the key 8 and the bit. The practitioner should alternately use the two hole sets 14 and 15, sliding the tenons 16 in the holes 14 or 15 making it possible to place the template 17 as close as possible to the bone to be drilled in order to obtain greater accuracy and avoid or reduce the amplitude of the vibrations of the bit.

In the position represented in FIG. 3, the template 17 makes it possible to drill into the jawbone, which already has the implant body 1, with a lateral hole aligned with the bore 6 of the body 1 (see FIG. 2). Once this hole has been drilled, the template 17 is then placed in a second position by releasing the tenons 16 from the holes 14 and introducing them into the holes 15 of the positioning tube 9. In this new position of the template 17, the guide bore 18 is in alignment with the bore 7 of the body 1 (see FIG. 2).

It is standard practice to market implants with an individual implant holder in sterile packaging. The part 9 provided with the screw 12 can be used as an implant holder and thus be delivered already mounted on the implant body 1. In this case, the rib 10 and the groove 5 become superfluous.

According to the variant represented in FIG. 4, the body 11 has, instead of the through-bores 6, 7 described above, blind bores 19, for example tapped, each intended to receive the free end, for example threaded, of a key 81.

The taps 19 may be arranged in the same plane, as represented, or alternatively in different planes.

Fitting the implant produced by means of the implant article according to the invention thus only requires the drilling of small-diameter lateral holes for passage of the key, while this implant also has the advantage of bearing both on the upper cortical bone (via the implant body) and on the lateral cortical bones (via the key).

Furthermore, since the mechanical linkages between the implant body and the transverse elements (keys) are linkages effected by cutting through the bulk of the implant body, the implant body is thereby securely locked in rotation about its axis (which corresponds to the axis of the well in which it is accommodated); in other words, the implant body can neither change its orientation relative to the other teeth nor pivot on itself.

The implant article according to the invention furthermore affords the practitioner the opportunity of adapting to the specific situation of the bone which he encounters, with a view to obtaining the best result in terms of quality of purchase. He may, for example, adopt a procedure whereby the key passes through a maximum compact bone thickness by suitably choosing the angular orientation of the implant body (and therefore that of the bore with which the latter is provided) relative to the jawbone.

Referring to FIG. 5, this figure shows a template 17', provided with its two sliding rods or tenons 16 and having, towards its lower end, instead of the passage 18, a tubular element 20 whose aperture 21 is equivalent to the passage 28. The free end of the tube 20 has a chamfer 22 allowing it to pass through the gingiva of the jawbone until it abuts against the bone. To this end, it is possible to drill the gingiva beforehand using a trocar guided in the passage 21. This thus ensures maximum accuracy for drilling the bone. The template may have a lower limb 23 used as a spacer for moving away the cheek of the patient.

Of course, various modifications may be made to the devices which have just been described, without thereby departing from the scope of the definition of the invention which is given by the appended claims.

We claim:

1. Dental implant article comprising:
   an implant body which is intended to be fitted in a substantially vertical cavity drilled into a jawbone from the upper face of the jawbone, said implant body having a bore substantially transverse to a longitudinal axis of said implant body; and
   an elongate key accommodated in said bore of the implant body, said key being intended to be fitted into the jawbone after the jawbone has been equipped with the implant body; and
   wherein said key is smooth and has a cylindrical shape and wherein said bore corresponds substantially to a cross-section of the cylindrical key for smooth sliding of said key in said bore.

2. Dental implant article according to claim 1, characterized in that said bore passes fully through said implant body.

3. Dental implant article according to claim 1, further comprising a plurality of said keys and wherein said implant body has a respective plurality of said bores located in different planes transverse to the longitudinal axis of the implant in such a way that said bores do not meet, each of said bores being intended to accommodate a respective one of said keys.

4. Dental implant article according to claim 3, characterized in that said bores are oriented in different directions.

5. Dental implant article according to claim 3 characterized in that said bores are oriented in parallel directions.

6. Dental implant article according to claim 1, characterized in that, at an upper end, said implant body has an alignment and fastening means for aligning and fastening of a positioning element, said positioning element being intended for mounting and positioning a template for drilling of a transverse hole in the jawbone for said key.

7. Dental implant article according to claim 6, characterized in that said alignment and fastening means is intended for fastening of a prosthesis on the implant.

8. Dental implant article according to claims 7, characterized in that said alignment and fastening means has an orienting means for angular location of said positioning element.

9. Dental implant article according to claim 1, characterized in that a plurality of said keys are provided with a same cross-section but with different lengths.

10. Dental implant article according to claim 1, characterized in that said bore is a blind bore of the dental implant in which said cylindrical key can be fixed.

11. Fitting device for fitting of a dental implant article into a jawbone, the dental implant article having (a) an implant body which is intended to be fitted in a substantially vertical cavity drilled into the jawbone from the upper face of the jawbone, the implant body having a bore substantially transverse to a longitudinal axis of the implant body and an alignment and fastening means at an upper end thereof, and (b) a smooth elongate key accommodated in the bore of the implant body, the key being intended to be fitted into the jawbone after the jawbone has been equipped with the implant body and having a smooth cylindrical shape corresponding substantially to a cross-section of the bore for smooth sliding of the key in the bore, said device comprising:

- a drilling template which can be temporarily secured to the implant body and which has a drilling guide means for guiding of a bit intended to drill into the jawbone a lateral hole for fitting of the key;
- a positioning element intended to be aligned with and fixed on the alignment and fastening means, said positioning element having a mounting means for interacting with the alignment and fastening means of the implant body; and
- an adjusting means for mounting said drilling template on said positioning element at adjustable positions and distances of said drilling template relative to said positioning element and hence relative to the implant body.

12. Fitting device according to claim 11, characterized in that the mounting means comprises a captive screw which is intended to be screwed into a blind tap of the implant body and cylindrically shaped alignment end part tart with a cross-section intended to correspond to that of a cylindrical opening of the implant body.

13. Fitting device according to claim 11, characterized in that the adjusting means comprises tenons extending parallel to a drill axis of the drilling guide means, and correspondingly shaped mortices in the positioning element intended to interact with said tenons in order to adjust the position of the template.

14. Fitting device according to claim 11, characterized in that said drilling guide means of said template includes a tubular element which guides the drilling bit and which said tubular element has a free end which is chamfered so that the free end can be applied against the bone to be drilled.

15. Fitting device according to claim 11, further including an orienting means for interacting with a means for orienting the implant in the implant body.

16. Dental implant article comprising:

- an implant body which is intended to be fitted in a substantially vertical cavity drilled into a jawbone from the upper face of the jawbone, said implant body having a bore substantially transverse to a longitudinal axis of said implant body; and
- an elongate key accommodated in said bore of the implant body, said key being intended to be fitted into the jawbone after the jawbone has been equipped with the implant body; and
- wherein said key has a smooth cylindrical shape ending in a threaded end, and wherein said bore is a tapped blind bore which accommodates said threaded end of the cylindrical key.

17. Fitting system for a dental prothesis comprising:

- an implant body which is intended to receive the dental prothesis, said implant body being fitted in a substantially vertical cavity drilled into a jawbone from the upper face of the jawbone, said implant body having a bore substantially transverse to a longitudinal axis of said implant body and an alignment and fastening means at an upper end thereof for the dental prothesis;
- a positioning element intended to be aligned with and fixed on said alignment and fastening means, said positioning element having a mounting means for interacting with said alignment and fastening means of said implant body; and
- a drilling template which has a drilling guide means for guiding of a bit intended to drill into the jawbone a lateral hole;
- an adjusting means for mounting said drilling template on said positioning element at adjustable positions and distances of said drilling template relative to said positioning element and hence relative to said implant body; and
- a smooth elongate key accommodated in said bore of said implant body and in the lateral hole drilled into jawbone after the jawbone has been equipped with said implant body, said key having a smooth cylindrical shape corresponding substantially to a cross-section of said bore for smooth sliding of said key in said bore.

18. Fitting system as claimed in claim 17 further comprising a plurality of said keys and wherein said implant body has a respective plurality of said bores located in different planes transverse to the longitudinal axis of the implant in such a way that said bores do not meet, each of said bores being intended to accommodate a respective one of said keys.

19. Fitting system as claimed in claim 18 characterized in that the mounting means comprises a captive screw which is intended to be screwed into a blind tap alignment end part with a cross-section intended to correspond to that of a cylindrical opening of the implant body (1).

20. Fitting system as claimed in claim 19 characterized in that the adjusting means comprises tenons extending parallel to a drill axis of the drilling guide means, and correspondingly shaped mortices in the positioning element intended to interact with said tenons in order to adjust the position of the template.

* * * * *